US00PP23026P2

(12) United States Plant Patent
Cunilio

(10) Patent No.: US PP23,026 P2
(45) Date of Patent: Sep. 11, 2012

(54) ***ARACHIS* PLANT NAMED 'ST. AUGUSTINE'S WHITE'**

(50) Latin Name: *Arachis glabrata*
Varietal Denomination: Fr. John's White

(76) Inventor: Thomas V. Cunilio, Gainesville, FL (US)

( * ) Notice: Subject to any disclaimer, the term of this patent is extended or adjusted under 35 U.S.C. 154(b) by 116 days.

(21) Appl. No.: 12/591,328

(22) Filed: Nov. 17, 2009

(51) Int. Cl.
*A01H 5/00* (2006.01)

(52) U.S. Cl. ..... Plt./258

(58) Field of Classification Search ..... Plt./258, Plt./263.1

See application file for complete search history.

(56) References Cited

OTHER PUBLICATIONS

Table of Contents. Turf Magazine. Aug. 2010. Available at: http://www.turfmagazine.com/issue-243.aspx.*
White, Patrick. "Peanut Power." Turf Magazine. Aug. 2010. Available at: http://www.turfmagazine.com/p[rint-5786.aspx.*
Burch, Derek. ed. The Master Plantsman Table of Contents Issue 10. Available at http://www.horticulturist.com/mastermag10/toc10.htm accessed Jul. 14, 2011.*
Davis, Todd. "Best of the Rest." The Master Plantsman Issue 10. Available at: http://www.horticulturist.com/mastermag10/best10.html accessed Jul. 14, 2011.*

* cited by examiner

*Primary Examiner* — Wendy C Haas
(74) *Attorney, Agent, or Firm* — MH2 Technology Law Group LLP

(57) ABSTRACT

A new and distinct cultivar of the *Arachis glabrata* plant named 'St. Augustine's White,' characterized by distinct, white flowers.

5 Drawing Sheets

Botanical designation: *Arachis glabrata.*
Varietal denomination: 'St. Augustine's White'.

BACKGROUND OF THE INVENTION

The present invention relates to a new and distinct cultivar of *Arachis* plant botanically known as *Arachis glabrata* and hereinafter referred to by the cultivar name 'St. Augustine's White.' *Arachis glabrata* is also commonly known as Rhizoma peanut or creeping forage peanut and is a high quality forage legume native to Brazil, Argentina, and Paraguay. It has also been introduced to other countries, including the United States, and can be used as an ornamental or for soil conservation. The normal flower color of *Arachis glabrata* is creamy yellow to yellow-orange. More specifically, by reference to the Munsell Color Chart for Plant Tissues, 1936 Edition, the normal flower color of *Arachis glabrata* ranges from 8 YR-Y 8/12 to 7 Y 8/12. A small amount of white color at the top of the standard, usually distributed in a spotted or blotchy pattern, is also observed in *Arachis glabrata.*

'St. Augustine's White' was discovered in Gainesville, Fla. as a naturally occurring whole plant mutation in a bed of cultivated *Arachis glabrata* germplasm known as "Arblick" (USDA PI 262839 and not patented).

Asexual reproduction by rhizome divisions of the new cultivar 'St. Augustine's White' first occurred in a controlled environment in at least 2002 in Gainesville, Fla. Since that time, under careful observation, the unique characteristic of the new cultivar has been stable and reproduced true to type in successive generations.

SUMMARY

The white flowers of the cultivar 'St. Augustine's White' have been repeatedly observed and represent the unique characteristic that distinguishes 'St. Augustine's White' as a new and distinct cultivar of *Arachis glabrata*. Other than the white flowers, the remainder of the 'St. Augustine's White' plant, including the rhizomes, roots, stems, and leaves, is indistinguishable from the wild type *Arachis glabrata.*

BRIEF DESCRIPTION OF THE DRAWINGS

The accompanying color photographs illustrate the distinguishing trait of the new *Arachis glabrata* cultivar 'St. Augustine's White.' All photographs were taken using conventional photographic techniques and although colors in the photographs may appear different from actual colors due to light reflectance, they are as accurate as possible by conventional photography.

DETAILED BOTANICAL DESCRIPTION OF THE PLANT

Figure 1:
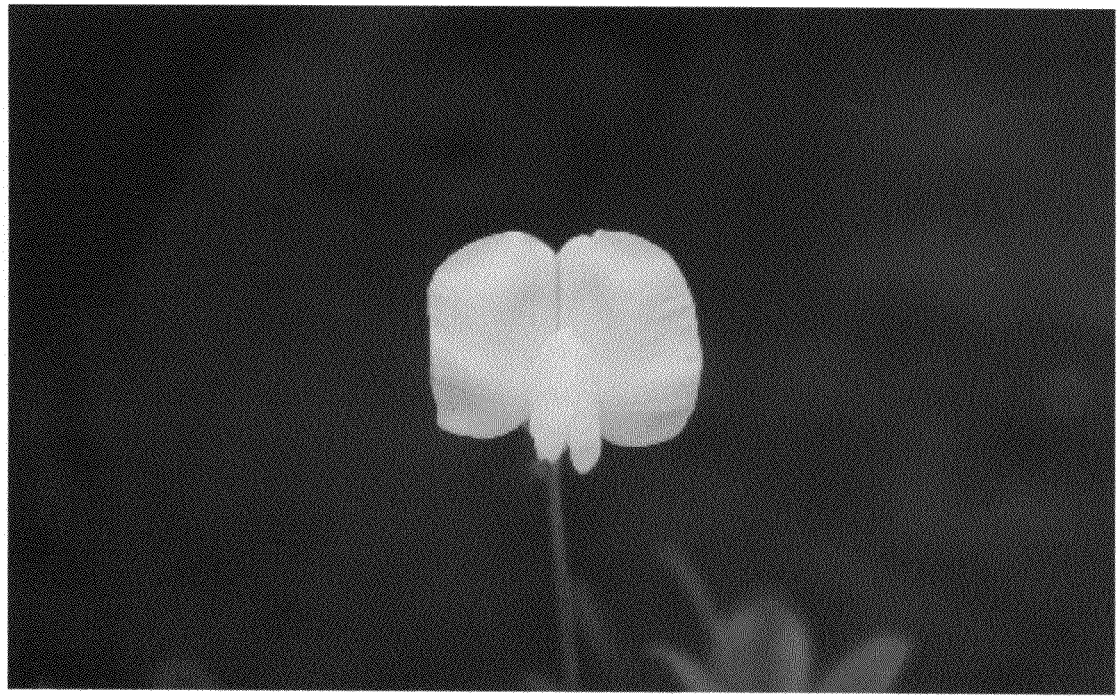
FIG. 1 shows a close up view of the normal creamy yellow to yellow-orange flower of wild type *Arachis glabrata.*
Figure 2:
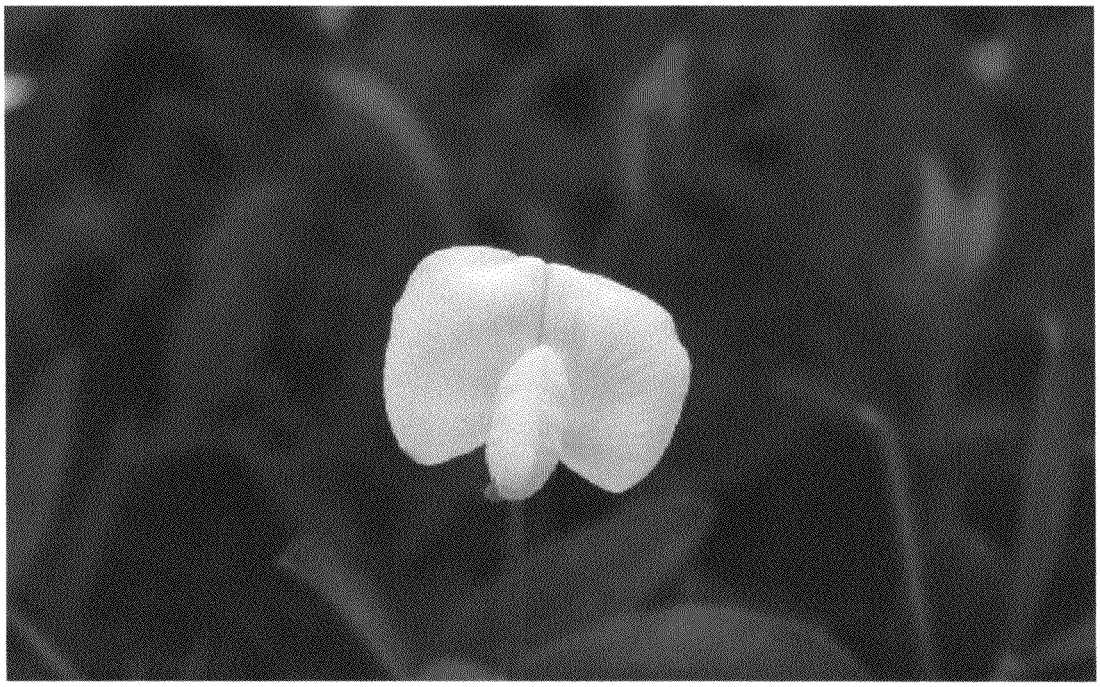
FIG. 2 shows a close up view of the white flower of the new *Arachis glabrata* cultivar 'St. Augustine's White.'
Figure 3:
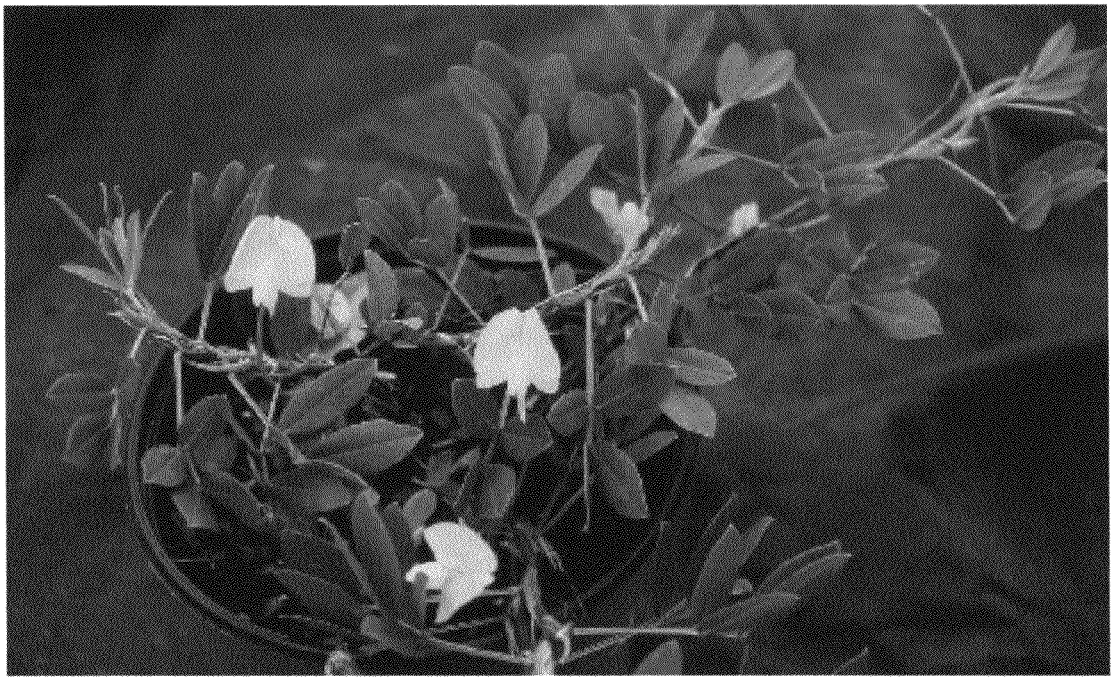
FIG. 3 shows a mid-range view of wild type *Arachis glabrata* grown in a mid-size pot, including the flowers, stems, and leaves.
Figure 4:
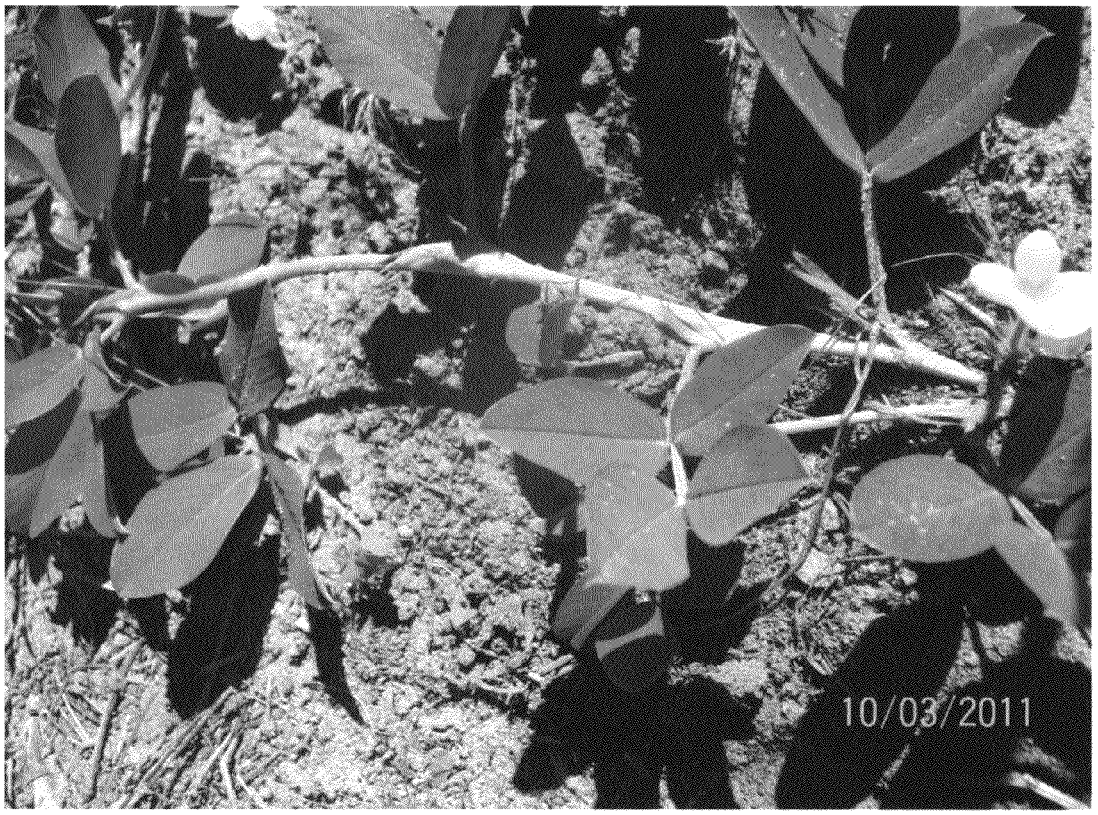
FIG. 4 shows a mid-range view of the new *Arachis glabrata* cultivar 'St. Augustine's White,' showing the stems, as well as the leaves and petioles.
Figure 5:
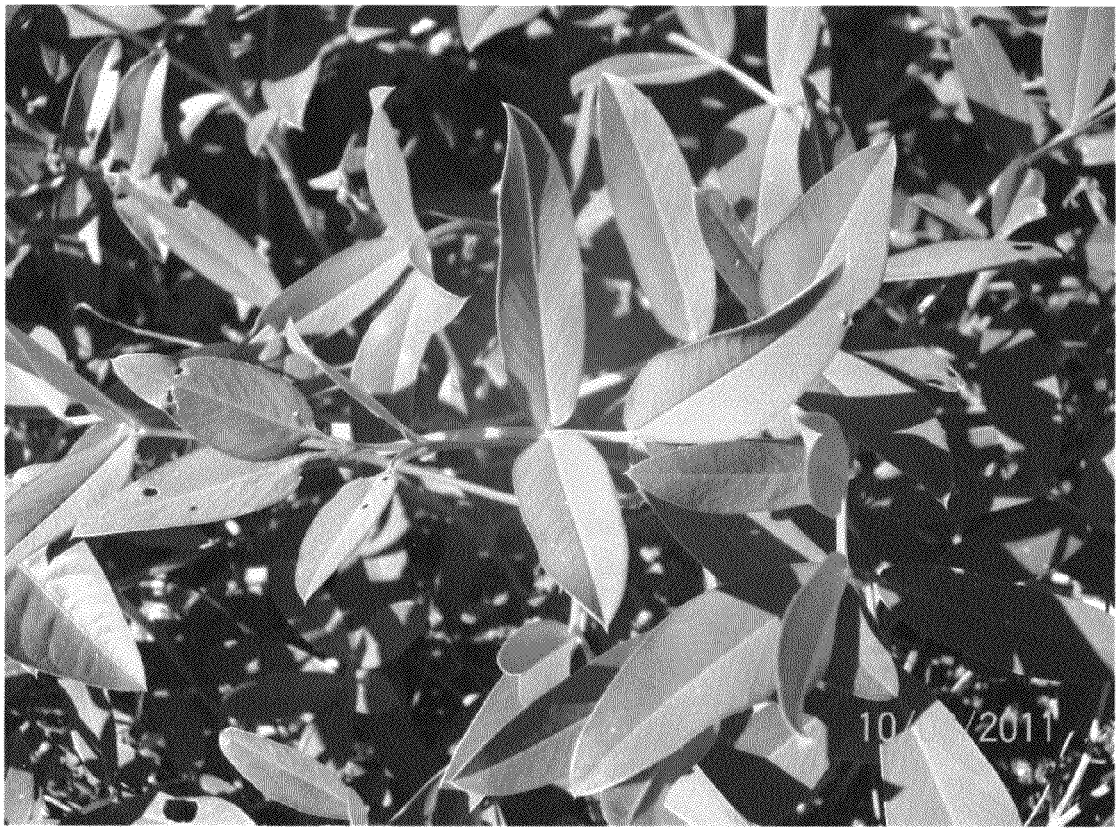
FIG. 5 shows a close up view of the new *Arachis glabrata* cultivar 'St. Augustine's White,' showing the leaves and petioles.

The following is a detailed description of the new *Arachis glabrata* cultivar named 'St. Augustine's White.' Data are representative of plants grown in a controlled environment in Gainesville, Fla., since about 2002 with low to medium fertility. The plants were grown outdoors in one gallon containers. Color references are made to the Munsell Color Chart for Plant Tissues, 1936 Edition, except where general color terms of ordinary dictionary significance are used. The photograph of 'St. Augustine's White' (FIG. 2) was taken of a plant grown indoors in a controlled environment with very high fertility, including foliar application of nutrients.

Botanical classification: *Arachis glabrata* cultivar 'St. Augustine's White.'

Parentage: 'St. Augustine's White' was discovered as a naturally occurring whole plant mutation in a bed of cultivated *Arachis glabrata* germplasm known as "Arblick" (not patented).

Propagation:

*Type*.—By rhizome divisions.

*Crop time*.—Approximately 14 to 16 weeks to produce a finished plant in a one gallon container from a rhizome division (approximately 8-10 weeks in 4 inch container).

*Root description*.—Strongly lignified roots; close to light to dark brown in color (y/YR 6/8).

*Rooting habit*.—Freely branching; moderately dense with strong tap roots.

*Rhizomes*.—Appearance: Only subterranean forming 1-3 inch thick, twisted mat. Shape: Elongate; rounded. Length: About 10 cm to 30 cm with stem nodes at 7 to 10 inch intervals. Diameter: About 3 mm to 5 mm. Texture: Smooth. Color: light to dark brown (y/YR 6/8).

Plant description:

*Type*.—Perennial.

*Plant habit*.—Low, spreading habit, from a central branching stem, forming single trifoliate shoots then stools 15-30 cm. (6-12 inches) in diameter in first year's growth.

*Plant height*.—Approximately 10-16 cm (4-6 inches) unsupported.

*Plant diameter*.—To 25-40 cm (10-15 inches) from a single nodal stem above ground.

*Growth rate*.—Slow but vigorous rhizomatous growth in well-drained sandy soils. Rhizome planting requires 3 years for complete coverage without irrigation.

Stem:

*Stem color*.—Greenish yellow (gY 7/10).

*Stem shape*.—Cylindrical except flat at apical leaf node.

*Internode length*.—2.5 to 4 cm. (1-1.6 inches).

*Stem width*.—1 to 2 mm. (0.4-0.8 inches).

*Stem length*.—5-38 cm (2 inch to 15 inches) unless climbing then to 50 cm (20 inches).

*Stem surface*.—Smooth.

*Stipules*.—Stipules small, relatively inconspicuous, linear-lanceolate or lanceolateacuminate, falcate, glabrous or sparsely pubescent when young forming a tube that covers one to two internodes.

*Branching habit*.—Primary branches are prostrate and creeping. Short, sub-erect, flower-bearing stems arise only from the nodes of the rhizome and typically extend above the leafy foliage.

Foliage:

*Appearance*.—The leaves contain 4-foliolate leaflets. Plants have 4 obtuse or retuse to acute leaflets per leaf on petioles. Leaflets are at most four times as long as wide, finely nerved usually becoming strongly reticulate beneath, the marginal nerve evident but not conspicuous, sometimes more or less pilose beneath and ciliate on the margins when young but usually becoming glabrous or nearly so at maturity. Petioles are greenish-yellow (g/Y 7/10).

*Length*.—Leaflet: About 6-35 mm (0.2-1.3 inches); Leaf: About 40-80 mm (1.6-3.3 inches).

*Width*.—Leaflet: About 5-14 mm (0.2-0.6 inches); Leaf: About 35-70 mm (1.4-2.8 inches).

*Shape*.—Obovate or oval to elliptical-lanceolate.

*Margins*.—Entire; thickened but not lignified.

*Texture*.—The blades are papyraceous or subcoriaceous, the lower surfaces and margins are glabrous or glabrata.

*Venation pattern*.—Parallel with central midrib.

*Color* (*upper and lower surface of leaflets*).—Yellowish-green (yG 5/6).

Flower:

*Flower type and habit*.—Single orbicular-shaped, sessile with no pedicel; flowers held upright and above foliage. Flowers axillary, arising up to a point above the middle of the stem.

*Natural flowering season*.—Flowers continuously from about April to November in Florida.

*Fragrance*.—None.

*Flower longevity on plant*.—One week unless fertilized. Fertilized flowers wilt 5-6 hours after expansion.

*Flower diameter*.—About 10-12 mm (0.4-0.5 inches).

*Flower length* (*height*).—About 7-10 cm (3-6 inches) from base of hypanthium to tip of standard.

*Flower depth*.—6.6 mm (0.25 inches).

*Corolla shape*.—Orbicular, emarginate at the apex and short-unguiculate at the base; wings oblong, obtuse; keel rostrate, curved upward.

*Number of petals*.—Single, notched, orbicular standard; two wing petals and a single keel that consists of two petals fused along their dorsal edges but are open ventrally at the base.

*Petal color*.—Standard and wings: 10 W 9.8/1. When grown in a controlled environment under conditions of very high fertility, it has been observed that a small, central portion of each wing petal and the top-most portion of the keel petals can have a weak yellow to orange tint (7 Y 6.5/3.5 to 7 Y 5.5/4.5).

*Receptacular* (*hypanthium*) *tube*.—Filiform, about 7-10 cm (3-4 inches) long and pilose.

*Calyx*.—Bilabiate, about 6-7 mm long, the upper lip with 3 or 4 nearly equal teeth and the lower entire, acuminate, and pilose. Color: greenish-yellow (gY 5/6).

*Calyx tube length*.—20-23 mm.

*Calyx tube diameter*.—1 mm.

*Calyx tube angle*.—Curved and 45 degree from vertical leaf axil.

Reproductive organs at anthesis:

*Stamen*.—Quantity: 8 functional — four double loculed, four globose and two sterile filaments. Dimensions: Stamenal tube: 3.2 mm. Color: yellowish red-Yellow (YR-Y 8/4 to 7/10).

*Anther*.—Shape: 4 types: globose; biloculate oblong, uniloculate oblong and sterile filaments; Dimensions: oblong anthers: 0.9 mm×0.3 mm; globose anthers: 0.3×0.3 mm. Color: yellowish red-Yellow (YR-Y 8/4 to 7/10).

*Pollen*.—Amount: Matures 6-8 hours before anthesis; approximately 300 pollen grains per plant. Color: yellowish red-Yellow (YR-Y 8/4 to 7/10).

*Pistil*.—Quantity: One per flower. Shape: Tubular; two sharp bends through the base of the standard/keel continuing down the center of the hollow hypanthium tube to the ovules in the leaf axil on the gynoecium ending with ovary at base. Dimensions: 7-10 cm (3-4 inches). Color: reddish-Yellow (rY 8/4 to 8/6).

*Stigma*.—Shape: feather or club-like with stiff, ascending hairs on the style below the stigma and facing the standard. Dimensions: 0.3 mm. Color: reddish-Yellow (rY 8/4 to 8/6).

*Style* (*hypanthium*).—Shape: tubular, filiform and elliptical in cross section; Dimensions: 7-10 cm (3-4 inches). Color: reddish-Yellow (rY 8/4 to 8/6).

*Ovary*.—Monocarpellate ovary is sessile and apparently terminal. Shape: Globose, 1 mm or less in length. Color: reddish-Yellow (rY 8/4 to 8/6).

Seed: Seed production is very rare in *Arachis glabrata* and has not yet been observed in 'St. Augustine's White' by the inventor.

Disease and pest resistance: Low susceptibility to insect attack.

Other: High drought tolerance and low frost tolerance. Not tolerant to permanently wet sites but can generally withstand submergence for up to two weeks.

It is claimed:

1. A new and distinct variety of *Arachis glabrata* plant named 'St. Augustine's White' substantially as shown and described.

* * * * *